United States Patent
Kalathil et al.

(10) Patent No.: US 10,449,143 B2
(45) Date of Patent: Oct. 22, 2019

(54) ALOE VERA EXTRACT FOR PERSONAL CARE COMPOSITIONS

(71) Applicant: Conopco, Inc., Englewood Cliffs, NJ (US)

(72) Inventors: Ramitha Kalathil, Bangalore (IN); Amitabha Majumdar, Bangalore (IN); Suman Majumder, Mumbai (IN); Jagannath Taduri, Bangalore (IN)

(73) Assignee: CONOPCO, INC., Englewood Cliffs, NY (US)

( * ) Notice: Subject to any disclaimer, the term of this patent is extended or adjusted under 35 U.S.C. 154(b) by 54 days.

(21) Appl. No.: 15/304,077

(22) PCT Filed: Apr. 2, 2015

(86) PCT No.: PCT/EP2015/057292
§ 371 (c)(1),
(2) Date: Oct. 14, 2016

(87) PCT Pub. No.: WO2015/158555
PCT Pub. Date: Oct. 22, 2015

(65) Prior Publication Data
US 2017/0035685 A1 Feb. 9, 2017

(30) Foreign Application Priority Data

Apr. 17, 2014 (EP) .................... 14165159

(51) Int. Cl.
| | | |
|---|---|---|
| *A61K 8/97* | (2017.01) | |
| *A61K 36/886* | (2006.01) | |
| *A61K 31/715* | (2006.01) | |
| *A61Q 19/00* | (2006.01) | |
| *A61Q 5/00* | (2006.01) | |
| *A61Q 11/00* | (2006.01) | |

(52) U.S. Cl.
CPC .............. *A61K 8/97* (2013.01); *A61K 31/715* (2013.01); *A61K 36/886* (2013.01); *A61Q 5/00* (2013.01); *A61Q 5/006* (2013.01); *A61Q 11/00* (2013.01); *A61Q 19/00* (2013.01); *A61Q 19/007* (2013.01); *A61K 2800/80* (2013.01)

(58) Field of Classification Search
CPC .............. A61K 2800/80; A61K 31/715; A61K 36/886; A61K 8/97; A61Q 11/00; A61Q 19/00; A61Q 19/007; A61Q 5/00; A61Q 5/006
See application file for complete search history.

(56) References Cited

U.S. PATENT DOCUMENTS

| | | |
|---|---|---|
| 4,735,935 A | 4/1988 | McAnalley |
| 5,723,673 A | 3/1998 | Kao et al. |
| 5,824,659 A | 10/1998 | Strickland et al. |
| 5,888,984 A | 3/1999 | Brown |
| 5,902,796 A | 5/1999 | Shand et al. |
| 6,436,679 B1 | 8/2002 | Qiu et al. |
| 6,482,942 B1 | 11/2002 | Vittori |
| 2002/0009438 A1 | 1/2002 | Shupe et al. |
| 2003/0096378 A1 | 5/2003 | Qiu et al. |
| 2004/0038931 A1 | 2/2004 | Elsobly et al. |
| 2005/0019433 A1 | 1/2005 | Van Dijk et al. |
| 2010/0255130 A1 | 10/2010 | DeBaun et al. |
| 2011/0172181 A1 | 7/2011 | Danhof |
| 2013/0129844 A1 | 5/2013 | Claret et al. |

FOREIGN PATENT DOCUMENTS

| | | |
|---|---|---|
| CN | 1418892 | 5/2003 |
| CN | 1424330 | 6/2003 |
| CN | 1948346 | 4/2007 |
| CN | 101693002 | 4/2010 |
| CN | 102101893 | 6/2011 |
| CN | 103622864 | 3/2014 |
| ES | 2224881 | 7/2006 |
| FR | 2932386 | 12/2009 |
| FR | 2924023 | 12/2010 |
| JP | 59013709 | 1/1984 |
| JP | 62263193 | 11/1987 |
| JP | 2000143527 | 5/2000 |
| KR | 19960037059 | 11/1996 |
| KR | 20120101897 | 9/2012 |
| WO | WO2006056801 | 6/2006 |
| WO | WO2012094010 | 7/2012 |

OTHER PUBLICATIONS

Amicon "Amicon Ultra 0.5 mL centrifugal filters: MWCO 3 kDA" Sigma-Aldrich (Millipore Sigma), Jun. 15, 2009, <URL: www.sigmaaldrich.com/catalog/product/aldrich/z677094?lang=en&region=US>, retrieved Apr. 1, 2018, 4 pages. (Year: 2009).*

(Continued)

*Primary Examiner* — Aaron J Kosar
(74) *Attorney, Agent, or Firm* — Foley & Lardner LLP

(57) ABSTRACT

The invention relates to a specific fraction of Aloe vera extract for enhancing tight junction in skin cells. The invention more particularly relates to use of such a fraction in skin, oral and hair care compositions. The inventive extract of Aloe vera comprises 60 to 95% by weight of polysaccharides having a molecular weight in the range of 2 to 3 kDa, and less than 5% polyphenols, wherein the polysaccharides are hydrolysed by trifluoroacetic acid.

13 Claims, No Drawings

(56) References Cited

OTHER PUBLICATIONS

Millipore, "Ultrafiltration Membranes: Ultrafiltration Membranes for Macromolecule Processing" Product Selection Guide, 2008, 5pp. (Year: 2008).*
Search Report and Written Opinion in EP14165157, dated Oct. 28, 2014.
Search Report for PCTEP2015057145, dated Jul. 28, 2015, WO.
Search Report in PCTEP2015057292, dated Sep. 15, 2015.
Written Opinion in PCTEP2015057145, dated Jul. 28, 2015, WO.
Written Opinion in PCTEP2015057292, dated Sep. 15, 2015.
Co-pending Application No.; filed Oct. 10, 2016.
Ouyang et al.; Food Research and Development, 2008, 29(11) ,pp. 153-156 (English Abstract).

* cited by examiner

ALOE VERA EXTRACT FOR PERSONAL CARE COMPOSITIONS

FIELD OF THE INVENTION

The invention relates to a specific fraction of Aloe vera extract for enhancing tight junction in skin cells. The invention more particularly relates to use of such a fraction in skin, oral and hair care compositions.

BACKGROUND OF THE INVENTION

People try to take good care of the external surface of their bodies as well as those of their pets to enable good overall health. Specific skin related issues that people care about include, good skin health free of infections, good skin tone and adequate moisturisation. Oral cavity is another external surface that people take active care to maintain. They prefer their oral cavity including the gums and teeth to be free of problems like cavities, tartar, gingivitis, caries, and bad breath, also known as halitosis, and plaque. Hair and scalp care are also of concern to people. People generally prefer to have thick long hair with minimum hair fall. Dandruff is a commonly occurring scalp problem for which a fungal microorganism has been implicated.

All of the above surfaces including skin, oral cavity and scalp hygiene are generally achieved by keeping them free of infections. One way to tackle infections is to treat them with antimicrobials after the infection has set in. Another approach is to leave a minimal amount of antimicrobial active on the surface so that any invading microorganism is killed or inactivated so as to minimize spread of disease. Yet another approach has been investigated by the present inventors which is the approach of improving the innate immunity of the desired surface.

The present inventors have found that a specific fraction of Aloe vera extract enhances inter-cellular tight junction in skin cells thereby providing enhanced moisturisation of skin and reducing chances of skin infections. The invention also relates to using such a fraction in oral care compositions for improved gum health and in hair care compositions for improving strength of hair fiber and also as a anti-dandruff agent.

FR 2932386 (Dohan David Marcel, 2009) discloses a composition based on natural extracts for oral, dermal or mucosa application in humans or animal. The composition comprises at least three original natural bioactive compounds (of plant, animal or mineral) possibly with additional ingredients, where the application is done by means of: gel, toothpaste, irrigation solution for ultrasonic instrumentation (in dental), mouthwash or lozenge or chewable on oral tissues (preferably on the gums the mucosa of the cheeks and back of the tongue); or gel, cream, applicator stick or rinse solution on the tissue surface (skin, mucous membranes).

U.S. Pat. No. 6,436,679 (UNIGEN INC, 2002) discloses a method for the preparation and isolation of biologically active polysaccharides from Aloe. This includes the activated mixture of polysaccharides (referred to herein as "Immuno-10"), produced by the methods of the invention. The cited art also includes the use of the polysaccharides as immunostimulating, immunomodulating and wound healing agents. The resulting immunomodulatory complex has a higher activity and is more stable than bulk carbohydrates isolated using prior art alcohol precipitation schemes.

CN1948346 (Yunnan, 2007) discloses a fractional extraction method of aloe polysaccharides, which comprises the steps of adding 8-10 times of 95 percent alcohol into concentrated Aloe product, letting it stand and precipitating after mixing, following by filtering, and collecting the Aloe crude polysaccharide. Thereafter water is added and mixed to dissolve the polysaccharide followed by gradually passing it through first an ultra-filtration membrane whose molecular cut off is 200000-4000, then passing it through a nano-filter membrane to concentrate it for getting Aloe polysaccharides of different molecular weight. This publication discloses Aloe fraction of higher molecular weight fractions as compared to the present invention and so the advantages of the present invention would not be obtained.

It is thus an object of the present invention to prepare an active that provides enhanced immunity to a topical surface of a human or animal body.

SUMMARY OF THE INVENTION

The present invention relates to an Aloe vera extract comprising 60 to 95% by weight of polysaccharides having a molecular weight in the range of 2 to 3 kDa; and less than 5% by weight polyphenols wherein the polysaccharides are hydrolysed by trifluoroacetic acid (TFA).

A preferred aspect of the present invention relates to a personal care composition comprising 0.1 to 10% by weight of the Aloe vera extract of the invention; and a cosmetically acceptable base.

Yet another preferred aspect of the present invention relates to a method of providing enhanced immunity to the external surface of a human or animal body comprising the step of applying a composition of the invention.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

By an extract is meant a material extracted from a plant source including fractions and derivatives of the extracted material. The extract is initially usually in a liquid form when extracted with a suitable solvent e.g. water. But the extract could thereafter be prepared in the solid form by separating the solvent from the liquid form of the extract.

By "A Personal Care Composition" as used herein, is meant to include a composition for topical application to the external surface of a human or animal body, preferably the human body and includes the skin, the scalp, the hair and the oral cavity. Such a composition may be generally classified as leave-on or rinse off, and includes any product applied to a human body for also improving immunity, appearance, cleansing, odor control, moisturisation or general aesthetics. It is preferably a leave-on product. The composition for skin care of the present invention can be in the form of a liquid, lotion, cream, gel, or toner, and may be applied with an implement or via a face mask, pad or patch. Preferably the composition is in the form of a cream, lotion or gel. "Skin" as used herein is meant to include skin on the face and body (e.g. neck, chest, back, arms, underarms, hands, legs, and buttocks).

The composition of the invention is also of relevance to applications on hair and scalp. The products for such application on scalp or hair generally provide benefits of providing strength to the hair fibre and for anti-dandruff benefits. Hair care compositions are delivered in the form of hair oils, hair care gels and creams and also in the form of wash off products like shampoos and conditioners.

The composition of the invention is also of benefit to oral care. Many oral care products like toothpaste, toothpowder, mouthwashes are of the wash-off type and in addition to these types of products, the present invention can be formulated in the form of gels, creams and ointments of the leave-on type for tooth and gum care.

The present invention relates to an extract of Aloe vera.

Aloe vera also known as Aloe barbadensis Miller belongs to the Liliaceae family, which contains hundreds of species. Aloe is found only in cultivation and has no naturally occurring populations. It is a stemless or very short-stemmed succulent plant growing up to a height of about 60 to100 cm. The leaves are thick and fleshy and appear in green to grey-green colour. Many of the health benefits associated with Aloe vera have been attributed to the polysaccharides contained in the gel of the leaves. A chemical analyses reveals that Aloe gel contains mannose polymers with some glucose and other sugars, among which the most important is Acemannan. Besides these, other components such as glycoproteins, enzymes, amino acids, vitamins, and minerals are known to occur. Extracts from Aloe vera are widely used in the cosmetics and alternative medicine industries, being marketed as having rejuvenating or soothing properties.

The leaf of Aloe vera is especially preferred for preparing the extract of the invention.

The Aloe vera extract useful for use in the present invention comprises (i) 60 to 95% by weight of polysaccharides having a molecular weight in the range of 2 to 3 kDa; and less than 5% polyphenols wherein the polysaccharides are hydrolysed by trifluoroacetic acid (TFA). Aqueous extract of Aloe vera generally available comprises 30 to 60% by weight polysaccharides having molecular weight of less than 10 kD and 10 to 20% by weight polyphenols. The present inventors have fractionated this extract to prepare a specific fraction having low molecular weight polysaccharides and much lower amount of polyphenols. The extract of the present invention preferably comprises less than 2% by weight polyphenols. They have further selectively hydrolysed this fraction by trifluoroacetic acid to substantially remove most of the side chain monosaccharides to prepare an active which is even further efficacious. The selective polysaccharides useful for the purposes of the present invention preferably comprise the polymer backbone:

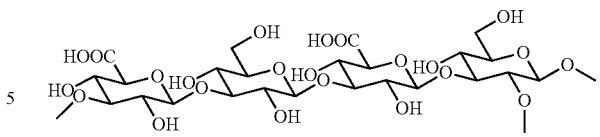

As a preferred aspect, the polysaccharide fraction of the extract comprises higher than 30% polysaccharides having the above polymer backbone. They have found that this fraction is very effective in enhancing tight junction for the purposes of the present invention.

Further, as a preferred aspect of the present invention there is provided an extract of Aloe vera obtainable using a process comprising the steps of
(i) extracting Aloe vera with water;
(ii) passing the extract through a 10 KD cut-off filter to obtain a low molecular weight fraction;
(iii) precipitating the polysaccharides in the low molecular weight fraction by addition of ethanol;
(iv) hydrolysing the polysaccharides with trifluoroacetic acid;
(v) removing the excess acid; and
(vi) precipitating the hydrolyzed polysaccharides using ethanol; and
(vii) drying the precipitate to yield the extract.

The trifluoroacetic acid is preferably removed from the mixture using the process of evaporation.

Without wishing to be bound by theory, the present inventors believe that the benefits of the present invention occur through enhancing Inter-cellular Tight junctions (TJs). Presence of TJs in epithelium enables it to act as barrier and stop the entry of pathogens and foreign substances into the human body. TJ is a multi protein complex made of trans-membrane and cytoplasmic proteins. TJ barriers are disrupted by pathogens and pathogens have evolved different strategies to remove the TJs and gain entry into host tissue. The major effect of loss of TJs due to pathogen infection can be seen in diseases like diarrhoea in the intestines and periodontitis in the oral cavity. Health and hygiene of the oral, gut and skin tissues depends on the stability of the TJs. The present inventors have prepared a specific fraction of an Aloe vera extract which interacts with the TJs thereby enhancing their stability and tightness to provide the benefits mentioned above.

According to a preferred aspect of the present invention there is provided a personal care composition comprising (i) 0.1 to 10% by weight extract of the invention; and
(ii) a cosmetically acceptable base.

The composition preferably comprises 0.1 to 5% by weight extract. The cosmetically acceptable base is such as to provide a product for skin, oral, hair or scalp care. The cosmetically acceptable base especially when prepared as a cream or lotion preferably comprises a fatty acid and optionally a soap of the fatty acid. When the fatty acid is present it is preferred to include it in 1 to 25%, preferably 3 to 20% by weight of the composition. When soap is is included it is preferably added at 0.1 to 10%, more preferably 0.1 to 3%. $C_{12}$ to $C_{20}$ fatty acids are especially preferred among the fatty acids for use in the composition of the present invention. Further more preferred fatty acids are $C_{14}$ to $C_{18}$ fatty acids. In creams, the fatty acid is preferably substantially a mixture of stearic acid and palmitic acid. Soaps in cream base include alkali metal salt of fatty acids, like sodium or potassium salts The soap is preferably the potassium salt of the fatty acid mixture. The fatty acid in vanishing cream base is often prepared using hystric acid which is substantially (generally about 90 to 95%) a mixture of stearic acid and palmitic acid. Thus, inclusion of hystric acid and its soap to prepare the composition is within the scope of the present invention. The cosmetically acceptable base is usually from 10 to 99.9%, preferably from 50 to 99% by weight of the composition. The cosmetically acceptable base preferably includes water. Water is preferably included in 35 to 90%, more preferably 50 to 85%, further more preferably 50 to 80% by weight of the composition.

When a skin or scalp care composition is prepared as a gel it primarily comprises high amount of water from 50 to 99% water which is thickened with one or more polymers. Polymers of natural or synthetic origin may be used. When of synthetic origin, it is preferably a polyacrylate polymer.

The skin or scalp care composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

When the composition is directed to oral care application, the cosmetically acceptable base is an orally acceptable base. The orally acceptable base is selected from water, calcium carbonate, silica or an orally acceptable surfactant. A preferred orally acceptable base is a mixture of water and surfactant. Preferred orally acceptable surfactant are an alkali metal alkyl sulphate or a betaine. The orally acceptable base depends on the format in which the oral care composition is delivered. The amount of orally acceptable base included in the composition of the invention also depends on the type if base included and is generally in the broad range of 0.05 to 99.9%, preferably 1 to 90%, further more preferably 5 to 70% by weight of the composition. Suitable formats of the composition as per the invention are an antiseptic mouthwash, a toothpaste or a toothpowder, preferably a toothpaste or a toothpowder.

Mouthwash

When the composition is formulated as an antiseptic mouthwash, the orally acceptable base is a mixture of water and surfactant. The antimicrobial mouthwash composition of the invention preferably comprises 0.05 to 10%, more preferably 0.05 to 8%, most preferably 0.5 to 5% of a surfactant by weight of the composition. The surfactant is preferably of the cationic, anionic, or zwitterionic class, most preferably of the cationic class. When anionic surfactant is present it is preferably chosen from alkali or alkaline earth metal salts of alkyl sulphonic acid, fatty acid, or alkyl ether sulphate. When zwitterionic surfactant is present it is preferably chosen from betaines, sulphobetaines, hydroxyl sulphobetaines, or amino carboxylates When a cationic surfactant is present it is benzalkonium chloride, alkyl pyridinium chloride or quaternary ammonium gemini surfactants.

Toothpaste

The composition of the invention may be delivered in a toothpaste format. When the composition is a toothpaste, the orally acceptable base is an abrasive which may be calcium carbonate or abrasive silica. When calcium carbonate is the abrasive, the toothpaste is in the opaque paste format. When abrasive silica is used, the toothpaste is usually delivered in the transparent gel format. Toothpastes also preferably comprise a surfactant in 2 to 15% by weight of the composition. Preferred surfactants are anionic or amphoteric in nature. Anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear C10-C18 chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Opaque Toothpaste

When calcium carbonate is the abrasive, it is usually present in 15 to 70%, more preferably in 30 to 60% by weight of the composition.

In addition to calcium carbonate, one can also include abrasive silica in opaque toothpastes for enhanced abrasive action. The abrasive silica may be included in 4 to 15%, preferably 6 to 12%, and further more preferably 7 to 10%. Alternatively perlite may be included in 0.0.1 to 2%, preferably in 0.1 to 0.8%, further more preferably 0.3 to 0.7% by weight of the composition.

Water in these toothpastes is generally included in 15 to 40%, preferably 20 to 30% by weight of the composition.

Preferred compositions include a humectant, e.g. xylitol, glycerol or sorbitol. Glycerol and sorbitol are particularly preferred. Preferably, the compositions include 0.1 to 20 wt % humectant. More preferred compositions include 1 to 15 wt % humectants while further preferred compositions include 5 to 13 wt % humectants.

Gel Toothpaste

Preferred compositions to prepare gel toothpaste comprise an abrasive silica. They preferably have a low refractive index in the range of 1.41-1.47, preferably 1.435-1.445, more preferably having a weight mean particle size of between 5 and 15 micrometer, a BET (nitrogen) surface area of between 10 and 100 $m^2/g$ and an oil absorption of about 70-150 $cm^3/100$ g. The amount of these silicas in the composition generally ranges from 2-60% by weight, usually 2-20% by weight and more preferably 5 to 12 wt %.

Thickening silica may also be incorporated in gel toothpastes. They are usually incorporated in 4 to 12%, preferably 5 to 10% by weight of the composition. Water in these toothpastes is generally included in 8 to 14%, preferably 8 to 10% by weight of the composition. These amounts of water are exclusive of water which are incorporated in the composition from aqueous solutions of other ingredients e.g. sorbitol.

The compositions for any type of toothpaste (opaque or gel type) may also include an anti-caries agent, binders, thickeners, flavours, stabilizing agents, polymers, vitamins, buffers and anti-calculus agents.

According to yet another aspect of the present invention there is provided a method of providing enhanced immunity to an external surface of a human or animal body comprising the step of applying a composition of the invention. By enhanced immunity is meant immunity better than that provided by conventional aqueous extract of Aloe vera.

According to yet another aspect of the present invention there is provided a personal care composition comprising 0.1 to 10% extract of the invention and a cosmetically acceptable base for providing enhanced immunity to an external surface of a human or animal body.

According to yet another aspect of the present invention there is provided use of the extract for imparting enhanced immunity to an external surface of a human or animal body.

According to yet another aspect of the present invention there is provided use of the extract of the invention in preparing the personal care composition of the invention.

The use is preferably non-therapeutic.

The invention will now be illustrated with the help of the following non-limiting example.

EXAMPLES

Examples A to D and 1, 2

Efficacy of Various Aloe Vera Fractions in Enhancing Inter-cellular Tight Junctions Various Aloe vera fractions were prepared as described below:

Preparation of Aloe Fractions:

Spray dried Aloe vera leaf gel powder (aqueous extract) was obtained from commercial sources. This was then dissolved in water. A less than 10 KD fraction was then prepared by size exclusion and centrifugation. This fraction was then concentrated to reduce the volume (approx. from 5 ml to 1 ml) and 5 times volume of ethanol was added to the solution to precipitate out the polysaccharides. The solution was then and allowed to stay for 30 minutes for complete precipitation. The solution was centrifuged to collect the precipitate. The precipitate was repeatedly washed with ethanol (3 times) and then dried to obtain an aloe polysaccharide fraction (F1).

F1 fraction was hydrolysed under reflux condition using trifluoroacetic acid (TFA) (1 g of F1 in 2.5 ml 2M TFA) for 2 hours. After hydrolysis, the solution was concentrated to dryness. TFA was completely removed by repeatedly stripping off by adding toluene/methanol.

To the dried material, 1.5 ml water was added to dissolve the material completely. 5 times the volume of ethanol was added to precipitate out partially hydrolysed polysaccharides. Polysaccharides were separated from this solution by centrifugation, repeatedly washed with ethanol and then dried to get the most preferred fraction which was designated as Fraction F2.

Example—A

'Control' Sample which indicates cells without any treatment.

Example—B

Cells were treated with 500 µg/ml concentration of an aqueous extract of Aloe vera gel power dissolved in water.

Example—C

Cells were treated with 500 µg/ml concentration of <10 KD fraction of Aloe vera gel power dissolved in water.

Example—D

Cells were treated with 500 µg/ml concentration of Fraction F1 (procedure to prepare it is as described hereinabove). The molecular weight of this fraction was around 2 KDa.

Example—1

Cells were treated with 500 µg/ml concentration of Fraction F2 as described hereinabove. The molecular weight of this fraction is around 2 KDa. The % of polysaccharides in this fraction was measured to be ~91%. The polyphenol content in this fraction was less than 2%.

The above samples were analysed for their ability to enhance inter-cellular tight junctions using the following procedure:

Measurement of TEER:

TEER stands for Trans Epithelial Electrical Resistance. This measures the stability of the tight junctions barrier. The procedure is as follows:

1. Millipore cell culture inserts (Millipore; cat no: PIHT12R48) were placed in a 24 well plate.
2. 500 µl of media were dispensed in the space within the well but outside the insert.
3. Keratinocytes (LONZA, cat no 192907) in KGM (LONZA, cat no: CC3111) were trypsinzes and resuspended. 80,000 cells/well (in 500 µl of media) were seeded into the inserts and incubated at 37° C. in 5% $CO_2$.
4. On day 1, the Trans Epithelial Electrical Resistance was measured (using Millicell ERS-2 Voltohmmeter from Millipore) in each of the wells. T
5. The used media from the wells were replaced with fresh KGM/actives (200 µl within the chamber and 800 µl outside the chamber) and incubated at 37° C. in 5% $CO_2$.
6. Steps 4-5 were repeated up to day 5.
7. The experiment was terminated by adding sodium hypochlorite (as a part of safe disposal of cells).

The data in the table shows the TEER values on Day 5, which correlates with the barrier stability at the end of day 5.

The data on the efficacy as measured using TEER value is summarised in Table—1.

TABLE 1

| Example | TEER values at Day 5 | S.D. |
|---------|----------------------|------|
| A.      | 99                   | 2    |
| B.      | 1159                 | 15   |
| C.      | 1271                 | 10   |
| D.      | 1270                 | 13   |
| 1       | 3156                 | 116  |

The data in Table—1 indicates that an Aloe vera fractions as per the invention (Example—1) provide for vastly enhanced tight junction enhancement indicative of improved immunity compared to various other fractions.

Another set of experiments were performed to distinguish the benefit of the fraction of the present invention with other fractions as disclosed below:

Example E

Cells were treated with 500 µg/ml concentration of F1 fraction (as described above) hydrolysed with cellulase. For this purpose TFA was replaced by the cellulase (Sigma, Cat. No. C1184) at the same concentration as described above.

Example F

Cells were treated with 50 µg/ml concentration of Aloe vera gel aqueous extract obtained after removing the less than 10 KD fraction as described in the previous section (greater than 10 KD fraction).

Example 2

Cells were treated with 500 µg/ml concentration of Fraction F2 as described hereinabove. The molecular weight of this fraction is around 2 KDa. The % of polysaccharides in this fraction was measured to be ~91%. The polyphenol content in this fraction was less than 2%.

The protocol of the experiments and the measurement of TEER value are same as mentioned above.

The results of these experiments are summarized below in Table 2:

| Example | TEER values at Day 5 | S.D. |
| --- | --- | --- |
| Control (only cells, no fraction) | 126 | 5.0 |
| E | 247 | 16.8 |
| F | 378 | 2.16 |
| 2 | 701 | 3.95 |

From the above table it is clear that Aloe vera fraction as per present invention (Example 2, which comprises TFA hydrolyzed polysaccharides) provide for much enhanced tight junction enhancement when compared with the Example E, F and G.

The invention claimed is:

1. A personal care composition comprising:
   a) 0.1 to 10% by wt. of an extract of Aloe vera comprising:
      (i) 60 to 95% by weight of hydrolysed polysaccharides having a molecular weight in the range of 2 to 3 kDa; and
      (ii) less than 5% by weight polyphenols;
      wherein the polysaccharides are hydrolysed by trifluoroacetic acid (TFA); and
   b) 10 to 99.9% by wt. of a cosmetically acceptable base which is selected from the group consisting of fatty acids, soaps of fatty acids, water and mixtures thereof;
   wherein higher than 30% by weight of said polysaccharides in the extract comprise the polymer backbone

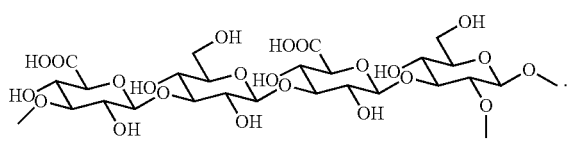

2. The composition of claim 1, wherein the extract comprises less than 2% by weight polyphenols.

3. The composition of claim 1, wherein the cosmetically acceptable base is selected from the group consisting of a fatty acid, an alkali metal salt of a fatty acid and water.

4. The composition of claim 3, wherein the fatty acid, an alkali metal salt of the fatty acid and water.

5. The composition of claim 4, wherein the fatty acid is present in an amount of from about 1% to about 25% by weight of the composition.

6. The composition of claim 4, wherein the fatty acid comprises $C_{14}$ to $C_{18}$ fatty acid.

7. The composition of claim 4, wherein the alkali metal salt of fatty acid comprises a sodium salt or a potassium salt of a fatty acid.

8. The composition of claim 4, wherein the alkali metal salt of a fatty acid is present in an amount of from about 0.1% to about 10% by weight of the composition.

9. The composition of claim 3, wherein water is present in an amount of from about 35% to about 90% by weight of the composition.

10. The composition of claim 1, comprising from about 1 to about 5% by wt. of an extract of Aloe vera.

11. An extract of Aloe vera comprising:
   (i) 60 to 95% by weight of hydrolysed polysaccharides having a molecular weight in the range of 2 to 3 kDa; and
   (ii) less than 5% by weight polyphenols;
   wherein the polysaccharides are hydrolysed by trifluoroacetic acid (TFA), and
   wherein higher than 30% by weight of said polysaccharides in the extract comprise the polymer backbone

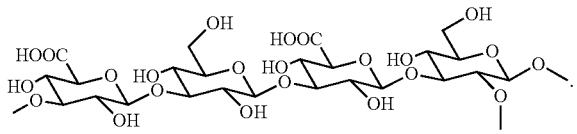

12. A method of providing enhanced immunity to an external surface of a human or animal body in need thereof, comprising the step of topically applying an effective amount of a composition as claimed in claim 1, wherein the external surface enhanced immunity provides a measurable change in trans-epithelial electrical resistance (TEER).

13. The composition of claim 1, having a trans-epithelial electrical resistance (TEER) value greater than the TEER value of compositions comprising Aloe vera extract not comprising 60 to 95% by weight of hydrolysed polysaccharides having a molecular weight in the range of 2 to 3 kDa.

* * * * *